US008967854B2

(12) United States Patent
Sand

(10) Patent No.: US 8,967,854 B2
(45) Date of Patent: Mar. 3, 2015

(54) SYSTEMS AND METHODS FOR MIXING AND DISPENSING FLOWABLE MATERIALS

(76) Inventor: Paul M. Sand, Redwood City, CA (US)

( * ) Notice: Subject to any disclaimer, the term of this patent is extended or adjusted under 35 U.S.C. 154(b) by 873 days.

(21) Appl. No.: 13/179,615

(22) Filed: Jul. 11, 2011

(65) Prior Publication Data

US 2012/0008455 A1  Jan. 12, 2012

Related U.S. Application Data

(60) Provisional application No. 61/399,425, filed on Jul. 12, 2010.

(51) Int. Cl.
*B01F 15/02* (2006.01)
*B01F 7/16* (2006.01)
*A61B 17/88* (2006.01)
*B01F 7/00* (2006.01)
*B01F 11/00* (2006.01)
*B01F 13/00* (2006.01)
*B01F 15/00* (2006.01)

(52) U.S. Cl.
CPC .......... *B01F 7/1695* (2013.01); *A61B 17/8833* (2013.01); *B01F 7/00116* (2013.01); *B01F 7/00158* (2013.01); *B01F 7/00208* (2013.01); *B01F 7/00291* (2013.01); *B01F 11/0054* (2013.01); *B01F 13/0028* (2013.01); *B01F 15/00506* (2013.01); *B01F 15/00525* (2013.01); *B01F 15/0279* (2013.01); *A61B 17/8827* (2013.01); *A61B 2017/8838* (2013.01); *B01F 2215/0029* (2013.01); *B01F 2215/0431* (2013.01); *B01F 2215/0477* (2013.01)
USPC ........................................... 366/189; 366/192

(58) Field of Classification Search
CPC .................... B01F 15/0272; B01F 15/0279
USPC ................................................. 366/189, 192
See application file for complete search history.

(56) References Cited

U.S. PATENT DOCUMENTS

| | | | | |
|---|---|---|---|---|
| 2,831,606 A * | 4/1958 | Alters | ............................... | 222/1 |
| 3,606,094 A * | 9/1971 | Mills et al. | ................. | 222/145.6 |
| 6,910,799 B2 * | 6/2005 | Renfro | ........................ | 366/169.1 |
| 8,191,729 B2 * | 6/2012 | Deusser et al. | ............... | 220/801 |
| 2009/0080284 A1 * | 3/2009 | Deusser et al. | ............... | 366/191 |

* cited by examiner

*Primary Examiner* — David Sorkin
(74) *Attorney, Agent, or Firm* — Brainspark Associates, LLC

(57) ABSTRACT

Disclosed herein are systems and methods for mixing materials together and transferring the materials into other instruments, particularly for use in the medical field.

19 Claims, 17 Drawing Sheets

SYSTEMS AND METHODS FOR MIXING AND DISPENSING FLOWABLE MATERIALS

FIELD OF THE INVENTION

The invention relates to systems and methods for mixing materials together and transferring the materials into other instruments, particularly for use in the medical field.

RELATED APPLICATIONS

This application claims the benefit of U.S. provisional application Ser. No. 61/399,425 entitled Device for Mixing and Dispensing Bone Cement, filed Jul. 12, 2010, the disclosure of which is incorporated herein by reference.

BACKGROUND OF THE INVENTION

Current methods and apparatus for mixing a plurality of materials together in the medical field, e.g., poly(methyl-methacrylate) bone cement comprising a powdered material with a liquid monomer to be used as a bone filling material, often yield unsatisfactory results.

Typically, in a surgical setting, the instruments employed for this purpose are a small bowl for receiving the components and a stick (such as a common tongue depressor) for mixing the components in the bowl. If a powdered material is employed, it is usually poured directly from its container into the bowl. Consequently, the process is often messy due to spillage of the powdered material. Where one of the components is a liquid monomer, the process can involve the release of noxious fumes released by the liquid monomer.

After the components are mixed, as in the case of a bone filling material, further problems are encountered. When the bone filling material is to be dispensed into a cavity in bone, the common practice is to first transfer the material into a syringe and then to transfer the material from the syringe into another instrument for delivery to the cavity. The syringe is loaded by either vacuuming up the material by withdrawing the fully engaged plunger through the syringe body, or by removing the syringe plunger and pouring the material into the back of the syringe and reinserting the plunger. This is a difficult and messy procedure, and there is often material loss from each step of the transfer (from spillage and/or residual material left in the dispensing bowl and/or lumens, etc.)

One example of a bone cement mixing and delivery system that provides some containment is shown in U.S. Pat. No. 5,193,907 to Faccioli et al. Faccioli discloses an apparatus for mixing and delivering bone cement formed from liquid and powder components. The apparatus comprises a cylindrical body and a plunger slidable within the body. A powder chamber stores the powder component between the plunger and a distal end of the body. A glass ampoule stores the liquid component inside the plunger. To mix the components, a user presses a plug in the plunger's proximal end to urge a tip of the glass ampoule against a cammed surface (or against a piercing member) to release the liquid component. The liquid component then passes through channels defined in the plunger's head to the powder chamber. The liquid and powder are mixed by shaking the body to form the bone cement mixture. After mixing, the plunger is pressed to discharge the bone cement mixture out of an exit port in the body and through a flexible conduit to a target site.

Another example of a bone cement mixing and delivery system is shown in U.S. Patent Publication No. 20100110820 to Coffeen et al. Coffeen et al discloses a battery-powered apparatus for mixing and delivering bone cement that utilizes the same motor to actuate both the mixing paddle and the transfer mechanism to minimize weight, cost, and waste, in a single use (disposable) system. According to Coffeen, the system and method of the present invention reduce user interaction compared to prior art devices and increases the readiness in which an operator can prepare a batch of bone cement for surgical purposes.

These prior art systems seek to reduce system set-up times, conserve a user's energy and/or reduce exposure of the user to the bone cement components. However, there is still a need in the art for bone cement mixing and delivery systems that have few components and are capable of mixing materials while containing the fumes and to easily and cleanly transfer and/or dispense the contents into other instruments.

SUMMARY OF THE INVENTION

Although various manufacturers of medical products have attempted to develop, manufacture and supply various systems for mixing and/or dispensing poly(methyl-methacrylate) bone cement (PMMA—e.g., DePuy—see PCT Publication No. WO97/21485, Immedica see PCT Publication No. WO99/37256, and Stryker—see U.S. Pat. No. 6,042,262) such systems are often expensive, too complex, require extensive and/or externally-powered accessories, or cannot mix small quantities of bone filler material. Because of these and other problems, there is a need for improved systems and methods for mixing and transferring materials, particularly in the medical field.

One aspect of the invention provides mixing and transfer systems that can be hand-held and/or disposable, if desired, as well as associated systems and methods for using the devices, which facilitate the accurate measurement of components before mixing as well as contain the components during mixing. Such systems also desirably mechanically mix and/or stir the bone filling material, and conveniently and cleanly transfer or dispense the mixture into other instruments. The systems provide a simple, quick and cost-effective way to mix and transfer materials.

Another aspect of the invention provides such systems and associated methods for using the systems which fully contain the components during mixing (desirably eliminating any significant spillage of noxious fumes released during mixing).

One aspect of the invention provides an assembly that includes a receptacle for receiving components, e.g., of a bone filling material, in an unmixed condition. The assembly also includes a mixing element connected to a cap that is securable to the receptacle to contain and mix the components therein. The assembly further includes an actuator for the mixing element. The actuator is desirably coupled to the mixing element. After a desired amount of mixing, the mixing element and cap can be removed, and a transfer and dispensing cap can be attached to the receptacle to transfer or dispense the mixture.

Another aspect of the invention provides a method for mixing and transferring a flowable material. The method provides a device for mixing and dispensing a bone filling material comprising a receptacle having a base and sidewall surrounding an interior for receiving components of the bone filling material in an unmixed condition. The method includes a mixing element and cap that secured, contains and mixes the bone filling material to a desired consistency. Once adequately mixed, the mixing element and cap are removed from the receptacle, and a transfer and dispensing cap is attached to the receptacle to urge the flowable material to a dispensing outlet of the transfer and dispensing cap. If desired, the system may be handheld, or a base the receptacle can support the receptacle in an upright condition and is sized and configured to resist tipping of the receptacle during use.

The method also provides a mixing element sized to be inserted into the interior of the receptacle with the mixing cap attached to the receptacle. In one embodiment, the mixing cap includes a flange which extends around and secures to the receptacle opening. Desirably, the flange extends along the longitudinal axis of a support rod attached to the mixing element, with the flange being larger in the longitudinal direction than the height of the mixing element. Desirably the support rod is free to rotate and displace relative to the mixing cap, with a sealing element between the support rod and the mixing cap. In use, with the mixing cap secured to the receptacle, the mixing element can be advanced downward into the receptacle to mix the flowable material in response to advancement and rotation of the support rod by a user. Once mixing is complete, the mixing cap and mixing element can be removed and sealed. A transfer and dispensing cap with attached plunger can then be attached to the receptacle, and the flowable material is dispensed.

The method places components of the bone filling material in an unmixed condition into the interior. With the receptacle desirably in an upright condition, the method manipulates the mixing element to mix the components of the bone filling material within the interior of the receptacle. Once completed, the mixing element is removed and a dispensing element is used to dispense the material.

In one embodiment, the mixing element comprises a mixing paddle or other device that mixes components in response to rotation and/or advancement/retraction. The mixing paddle can include a structure to promote mixing of components, such as, e.g., a plurality of apertures. In this arrangement, the actuator includes a drive member that rotates the mixing paddle. In various embodiments, the actuator can include a automatic or manual drive train, e.g., a powered mixing device and/or manual planetary gear train that couples a drive member to a driven member. In various embodiments, the drive member can be operated manually such that no external power source is required.

DETAILED DESCRIPTION OF THE EMBODIMENTS

The embodiments described herein describe systems and methods that embody features of the invention in the context of mixing a bone filling material. It should be appreciated, however, that the systems and methods so described are not limited in their application to the mixing of bone filling material. The systems and methods are applicable for use in diverse applications, both inside and outside the medical field.

It should also be appreciated that the various component parts of the inventions described herein can be comprised of plastics, ceramics, composites, non-ferrous and/or non-metallic materials, which would permit the various embodiments to be utilized in a magnetic and/or whole room MRI environment.

I. The Component Parts

Figure 1:
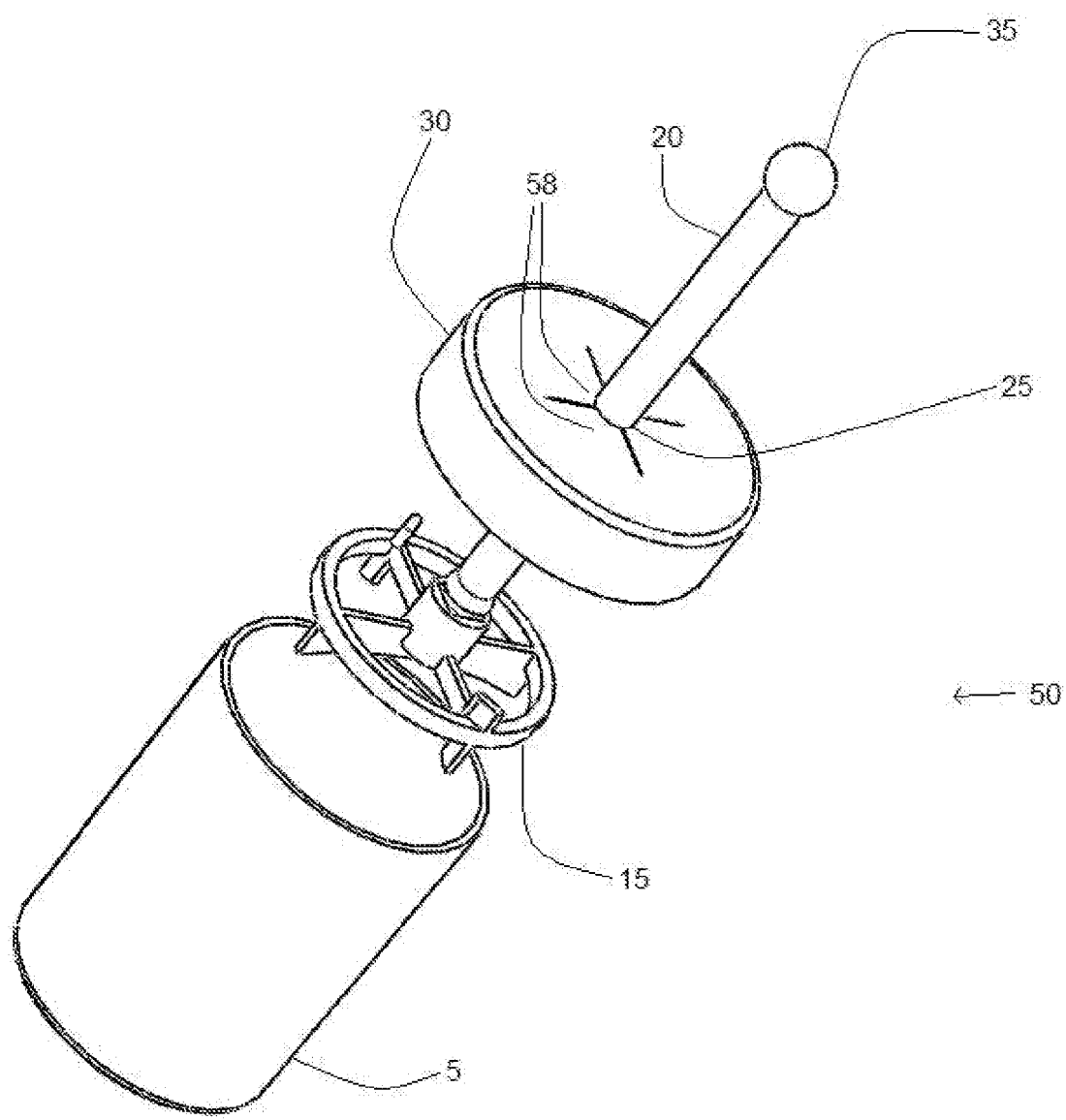
FIG. 1 depicts an exploded perspective view of one embodiment of a mixing system.
Figure 2:
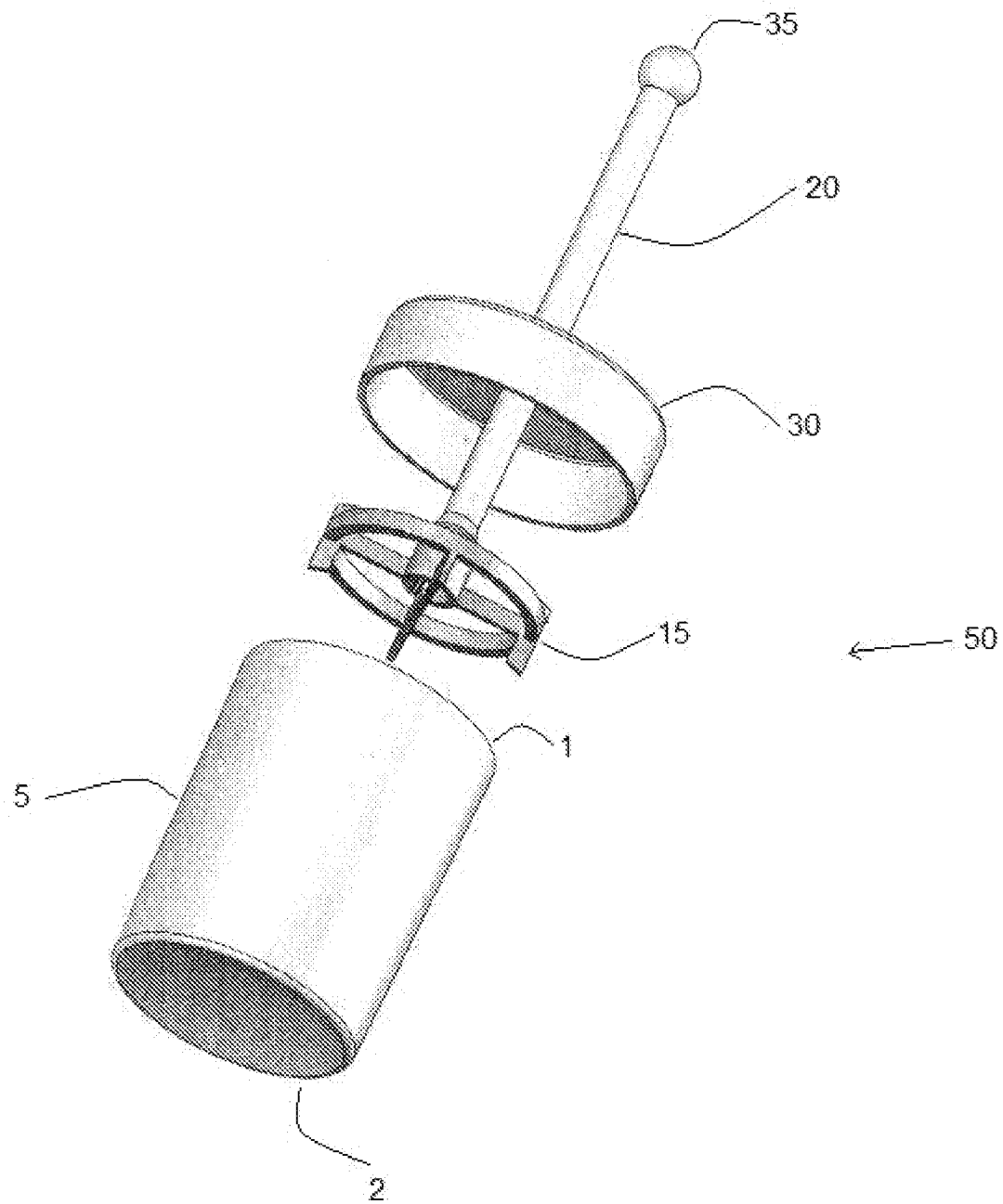
FIG. 2 depicts another exploded perspective view of the embodiment of a mixing system from FIG. 1.

FIGS. 1 and 2 show component parts of a mixing system 50. The components of the system are usable in association with each other to form a material mixing and transferring system. The number and structure of the component parts can vary. In FIG. 1, the mixing system 50 includes a receptacle 5 for receiving and containing materials for mixing and for, after mixing, transferring or dispensing the materials. A stand (not shown) is optionally provided to hold and/or secure the receptacle 5. A mixing element 15 is desirably sized and configured to be inserted into the receptacle 5 to mix materials contained therein. A mixing rod 20 is attached to the mixing element 15 and extends through an opening 25 in the mixing cap 30. One or more seals (not shown) are positioned between the walls of the opening 25 and the mixing rod 20, and comprise various known sealing materials, including latex rubber. The seals will desirably permit rotation of the mixing element and rod 20 relative to the cap 30 while maintaining a substantially air-tight seal between the receptacle contents and the atmosphere. In addition, the sliding seal desirably permits longitudinal movement/translation of the rod within the cap.

A knob 35 or grip or other actuating device is attached to a proximal end of the rod 20. The knob is desirably textured or otherwise knurled to allow an individual to grip and turn the knob 35 while wearing latex or other gloves (desirably as part of a sterile field in an OR environment). In alternate embodiments, the knob 35 or rod 20 may include a docking feature for attachment to a mechanically or electrically powered drill or other device for mixing the material. If desired, the cap 20 may include one or more flexible flaps 58 that permit the knob and upper portion of the mixing rod 20 to be pushed through the cap 20. Such an arrangement facilitates assembly of the device from it's component parts, which can be more conveniently stored and/or shipped in an unassembled form.

Additional components for the mixing system (not shown) may include measuring and/or transfer devices (i.e., measuring cups, etc.) for measuring components and/or dispensing them into the receptacle. A measuring device can be used to measure components before placing the components into the receptacle for mixing. The measuring device may be of a fixed size, such as a 10 cc, 20 cc or 50 cc measuring cup, may be graduated and include one or more transparent sections, and/or may include a sieve for sifting particles before mixing.

A funnel can be used to facilitate placing or pouring of component materials to be mixed into the receptacle. If desired, additional powdered materials, such as sterile barium sulfate (to make the mixture radiopaque) or antibiotics (to prevent infection) may be added to the receptacle before addition of the liquid monomer.

Desirably, the components of the system can comprise a substantially rigid metal, plastic or ceramic material. In one embodiment, the components comprise polypropylene, and the receptacle 5 comprises Acetal homopolymer (DELRIN® material from DuPont Corporation) or a clear or colored nylon. The component materials will desirably be unaffected by contact with the bone filler material and/or sterilizable by gamma radiation. Of course, various other alternative materials can be used, including materials which are capable of withstanding contact with monomer without significant degradation for limited periods of time (such as, for example, the amount of time they are used to mix and dispense the material).

A. The Receptacle

Figure 15A:
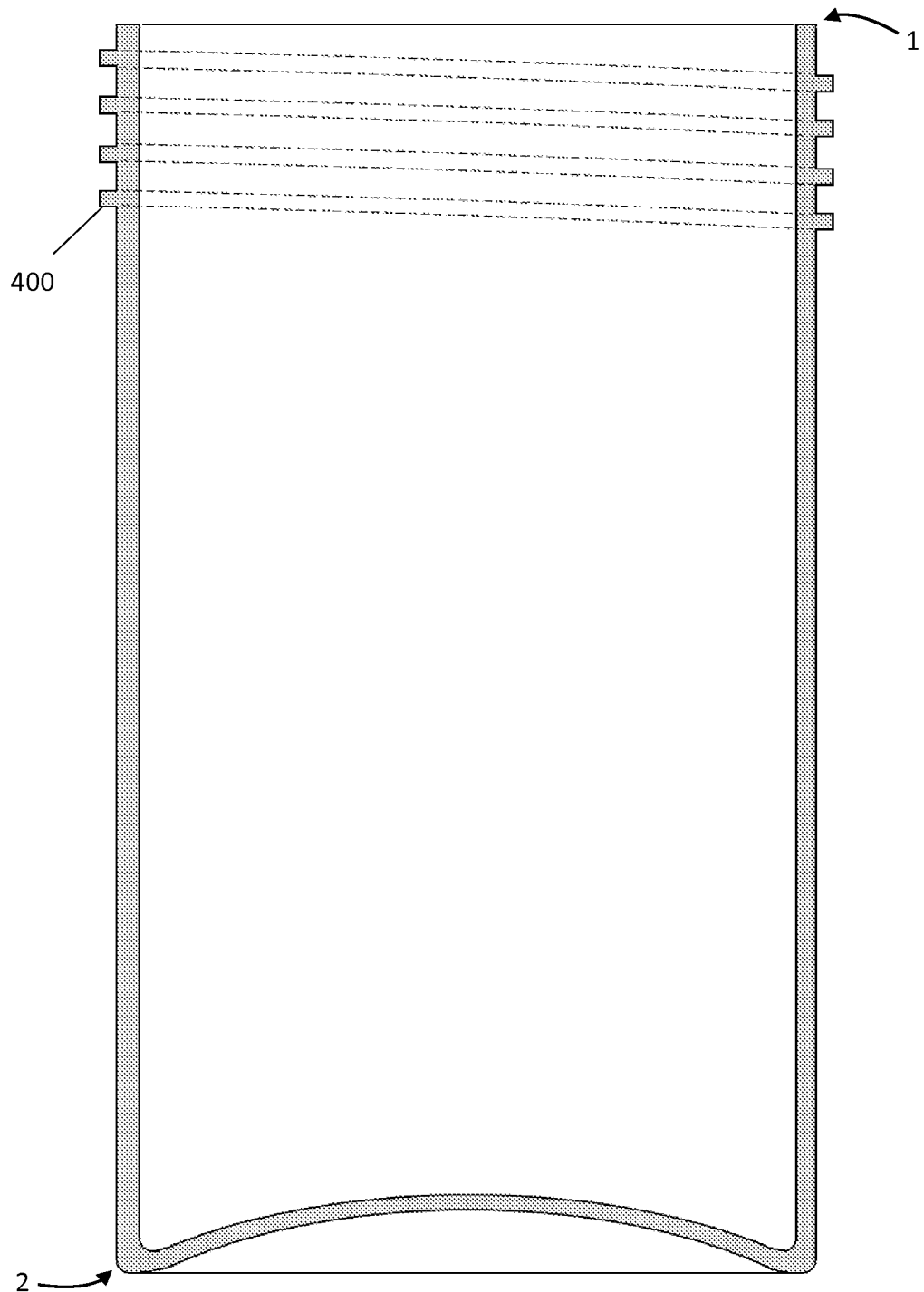
FIG. 15A depicts a cross-sectional view of one alternative embodiment of a receptacle.
Figure 15B:
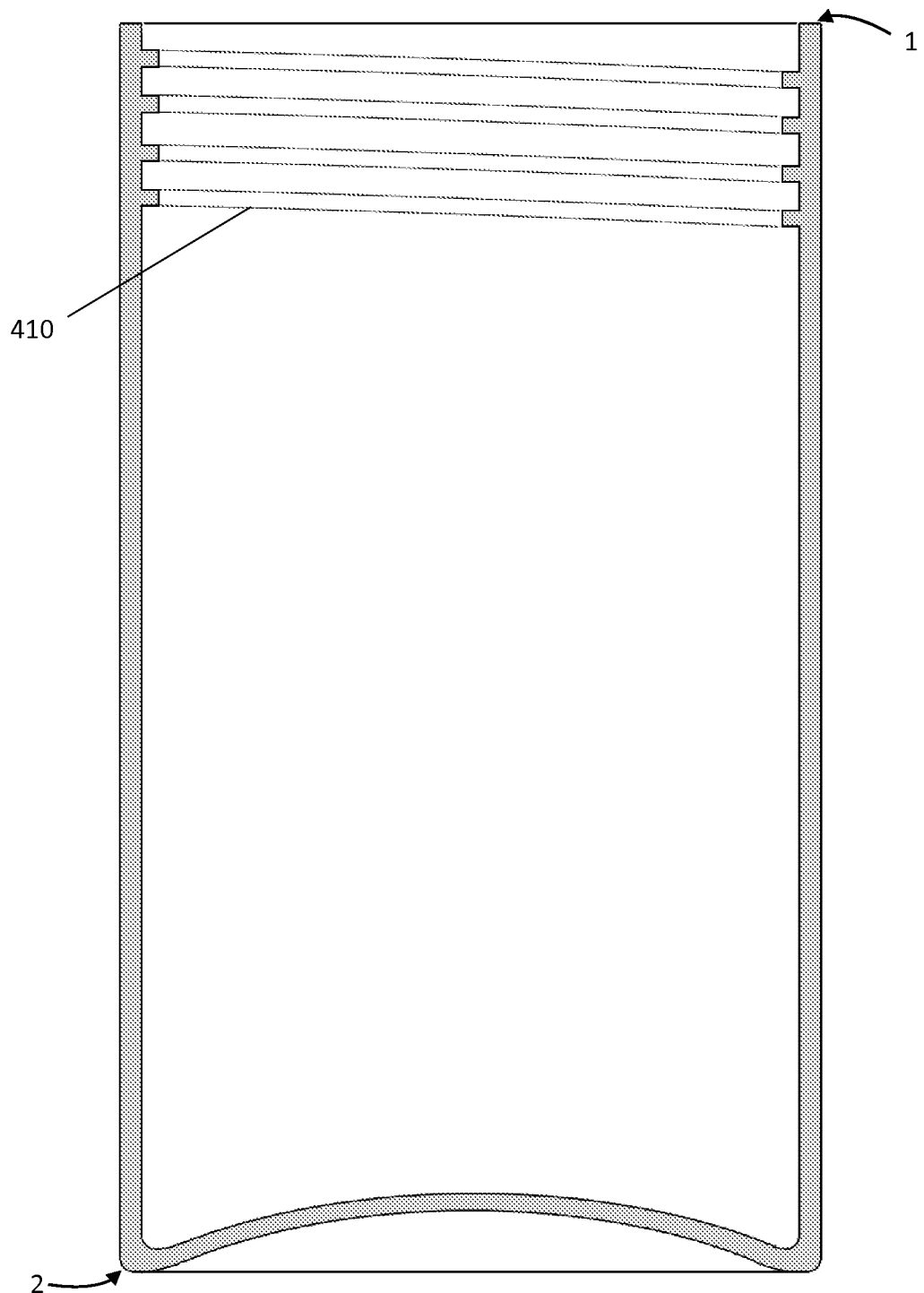
FIG. 15B depicts a cross-sectional view of another alternative embodiment of a receptacle.

The receptacle 5 has a proximal end 1 and a distal end 2. The receptacle 5 further has an interior bore which desirably extends from the proximal end. The distal end 2 of the receptacle is closed. In various embodiments, an external thread 400 or internal thread 410 (see FIGS. 15A and 15B) or other securing arrangement is provided on the proximal end 1 of the receptacle. Desirably, the bore is of constant diameter, although numerous shapes and/or sizes of bores that could accommodate the mixing element would have varying utility.

Figure 15C:
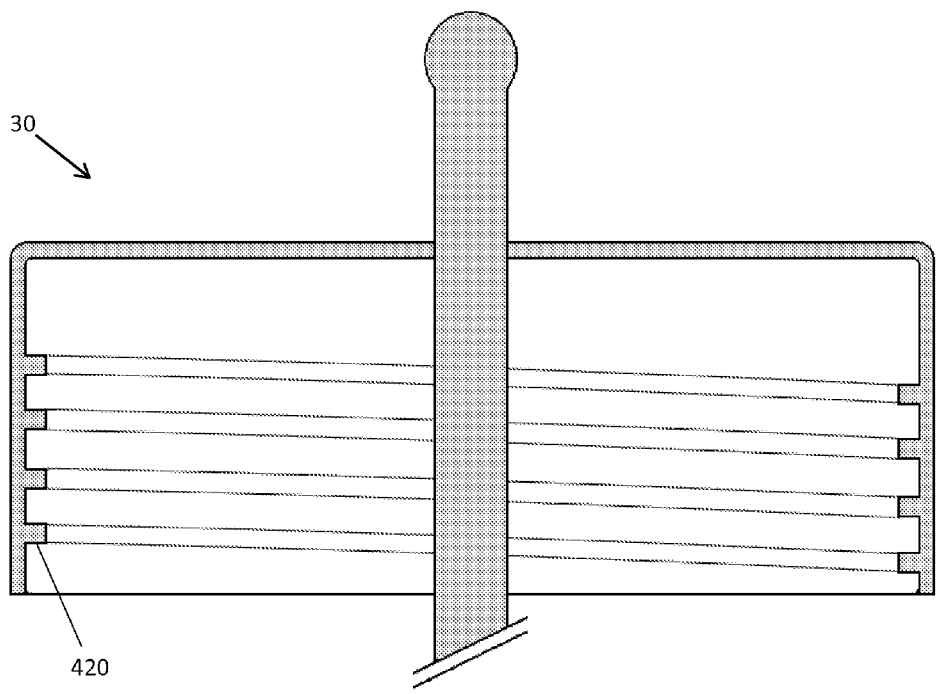
FIG. 15C depicts a cross-sectional view of one exemplary embodiment of a mixing cap and partial plunger.

The receptacle 5 is sized to accommodate the mixing element 15. The interior surface of the closed distal end 2 is desirably curved and sized to support the mixing element 15 during use, as will be described in greater detail later. The threads or other securing arrangement on the proximal end 1 of the receptacle desirably interact with corresponding threads 420 (see FIG. 15C) on the mixing cap 30, allowing the cap 30 to be secured to the receptacle 5 as desired. Of course, other fasteners, including bayonet fittings, snap-fits and/or a compression or o-ring type seal, could be used between the cap 30 and the receptacle 5. The mixing element 15 is attached to a mixing rod 20. The mixing rod 20 extends through an opening 25 in the mixing cap 30. A knob 35 or other actuating device is attached to a proximal end of the rod 20.

The various components of the present invention may be molded in a unitary article or components may be connected using snap fits and/or by welding and/or by adhesive or by other means known in the art.

In one embodiment, the receptacle 5 has a volume of approximately seventy cubic centimeters (70 cc). Of course, other size receptacles 5 could be used, depending upon the size of the mixing element 15 and other associated components, and the desired amount of filler material to be mixed. Other representative sizes could include five (5), ten (10) and twenty (20) cc volumes. In various embodiments, the outer surface of the receptacle 5 could include a graduated scale or other indicators showing the volume of material (either mixed or unmixed) inside the receptacle 5. Preferably, the graduated scale would begin near the distal end 2 of the receptacle 5. In this embodiment the receptacle 5 could desirably be made of transparent polypropylene to allow viewing of the materials to be mixed when placed in the receptacle 5, during mixing and/or during dispensing/transfer.

In one alternative embodiment, the receptacle 5 could include a stand or other holding device at the distal end 2, which could comprise a receptacle base (not shown). The stand would desirably accommodate the cylindrical distal end 2 of the receptacle 5. The stand desirably stabilizes the receptacle 5 to provide a solid footing to minimize tipping of the receptacle 12 and allow it to be rested on a flat surface.

The stand may be a separate component from the receptacle, or may be formed integrally with the receptacle.

If desired, one alternate embodiment of the receptacle 5 may incorporate a vacuum attachment (not shown) for a standard operating room suite vacuum hose, to evacuate fumes in the receptacle and/or degas the material. Alternatively, the mixing cap can incorporate a vacuum hose attachment. If further desired, the receptacle may form a cartridge for a bone filling material delivery gun.

B. The Mixing Element

Figure 3:
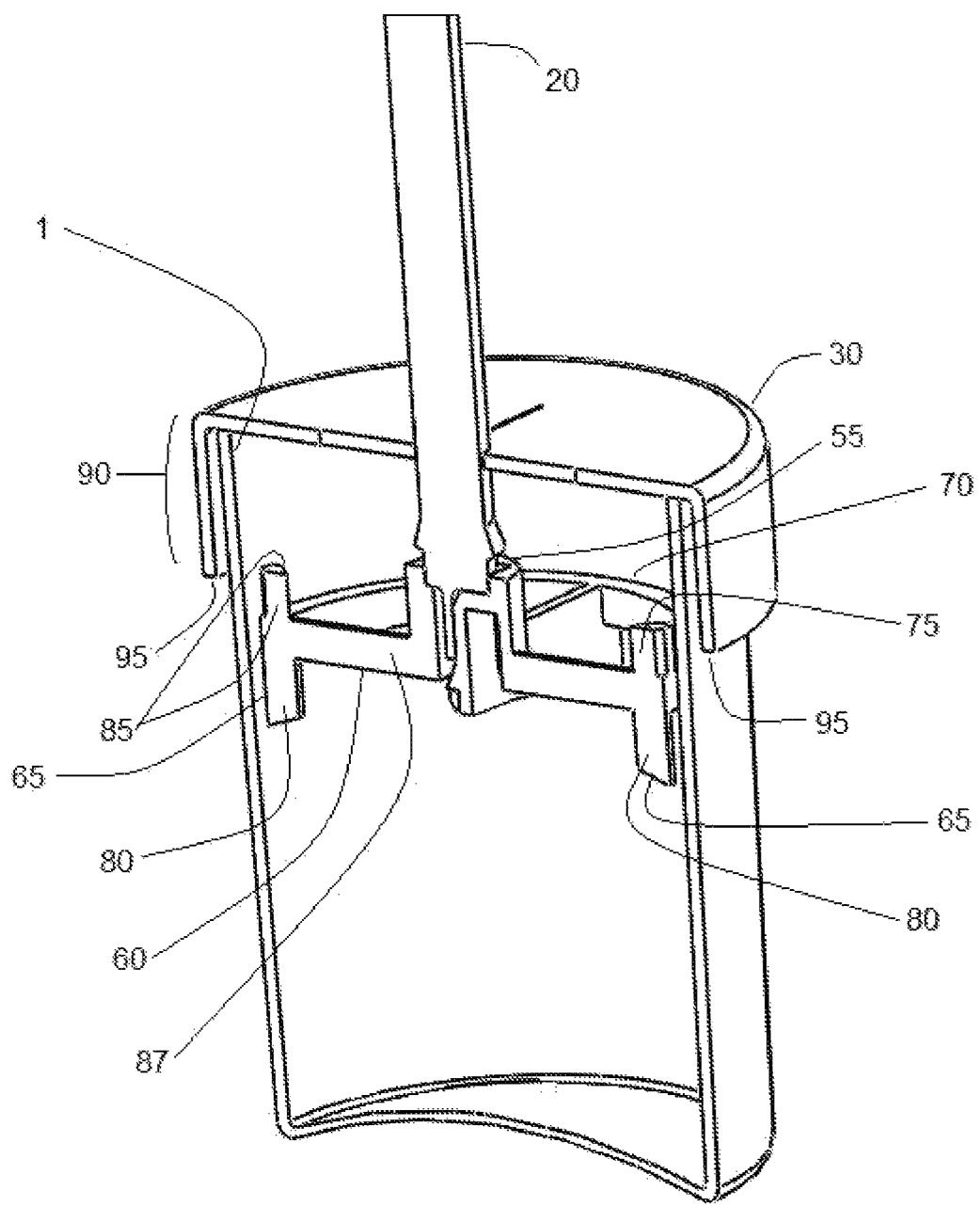
FIG. 3 depicts a cross-sectional view of the mixing system of FIGS. 1 and 2.

The mixing element 15 can be variously configured. As best seen in FIG. 3, the mixing element 15 comprises a central shaft 55 attached to the mixing rod 20. A series of axles or spokes 60 extend outward from the central shaft 55 to one or more mixing paddles 65. A collar 70 or rim extends around the interior periphery of the receptacle 5, and desirably attaches to each of the paddles 65. Each paddle 65 desirably has an upper flange 75 and a lower flange 80. In the disclosed embodiment, each flange presents a beveled face 85 to the direction of rotation of the mixing element 15, which desirably "wipes" material from the inner wall of the receptacle 5, forcing it towards the center of the receptacle 5 for further mixing. In the disclosed embodiment, each axle 60 presents a relatively flat face 87 toward the direction of rotation of the mixing element 15, which desirably agitates and mixes material within the receptacle 5. In addition, the collar 70 desirably interacts with the inner wall of the receptacle 5 such that, when advanced or withdrawn from the receptacle, the rim "wipes" material from the inner surface of the receptacle 5. In use, the mixing element 15 desirably rotates and/or longitudinally advances/retracts within the receptacle 5 to mix the materials contained in the receptacle 5.

In the various described configurations, the lower flanges 80 of the mixing element 15 are desirably beveled or angled such that, when the mixing element 15 is fully advanced into the receptacle 5, the lower flanges 80 wipe or scrape against the lower corners and/or bottom of the receptacle, desirably urging unmixed and/or partially mixed material back towards the center of the receptacle 5. If desired, the mixing element 15 may also include one or more crosswise ribs or other supports (not shown), as well as flanges that extend the full length of the axle/spoke to allow for better wiping and/or greater strength of the mixing element.

The components of the mixing element 15 are desirably sized and configured to allow some of the mixture to flow around the various components, thereby allowing the mixing element 15 to rotate relatively freely within the receptacle 5 with a minimum of resistance and maximizing the mixing of the chosen mixing materials. As the size and coverage of the various components increase (such as, for example, increasing the cross-sectional area of the flanges in the direction of rotation of the mixing element 15), greater resistance to rotation would typically be noted, along with a greater amount of mixing and/or gross movement of the mixed material. As the mixture polymerizes and thickens, however, there may be greater resistance to mixing, requiring additional forces that could exceed the strength of the components of the mixing element 15. Less resistance, therefore, may provide adequate and thorough mixing, while reducing or eliminating unacceptable levels of resistance.

In one embodiment, the combined height of the upper and lower flanges 75 and 80, are equal or less than the internal height of a lip 90 of the mixing cap 30. When mixing is complete, and the mixing cap 30 removed from the receptacle 5, this arrangement allows the mixing element 15 to be withdrawn fully within the lip 90 of the mixing cap 30 (by pulling upwards on the mixing rod 20), with a beveled step 57 on the rod 20 pulling through and engaging with a flexible flap 58 of the cap 20. This secures the mixing element within the cap and facilitates placement of the lower edge 95 of the mixing cap 30 flush onto a flat surface. Desirably, the lower edge 95 in contact with a surface (not shown) will effectively "seal" the interior of the mixing cap 30 closed, thereby reducing the further release of fumes from any mixed material still resident on the mixing element 15. Because the mixed material on the mixing element 15 may contact the surface as well, and likely continue to polymerize, it is desirable to place the mixing cap on a disposable surface, such as large gauze pad, such that the mixing cap and gauze may be disposed of when polymerization of the material is complete (and the cap and gauze may be adhered together).

In one alternate embodiment, the mixing cap 30 could include an integral disposal cap (not shown), which may be attached to the cap 30 by a cord or by a "living hinge," as is known in the art. Once the cap 30 is removed from the receptacle 5, the disposal cap could be inserted into the mixing cap 30, or the cap 30 could be placed onto the disposal cap or other disposal feature (such as, for example, a small flat plate), and the material allowed to further polymerize and/or the cap and associated elements disposed of immediately with little additional release of fumes and/or mess.

Figure 4:
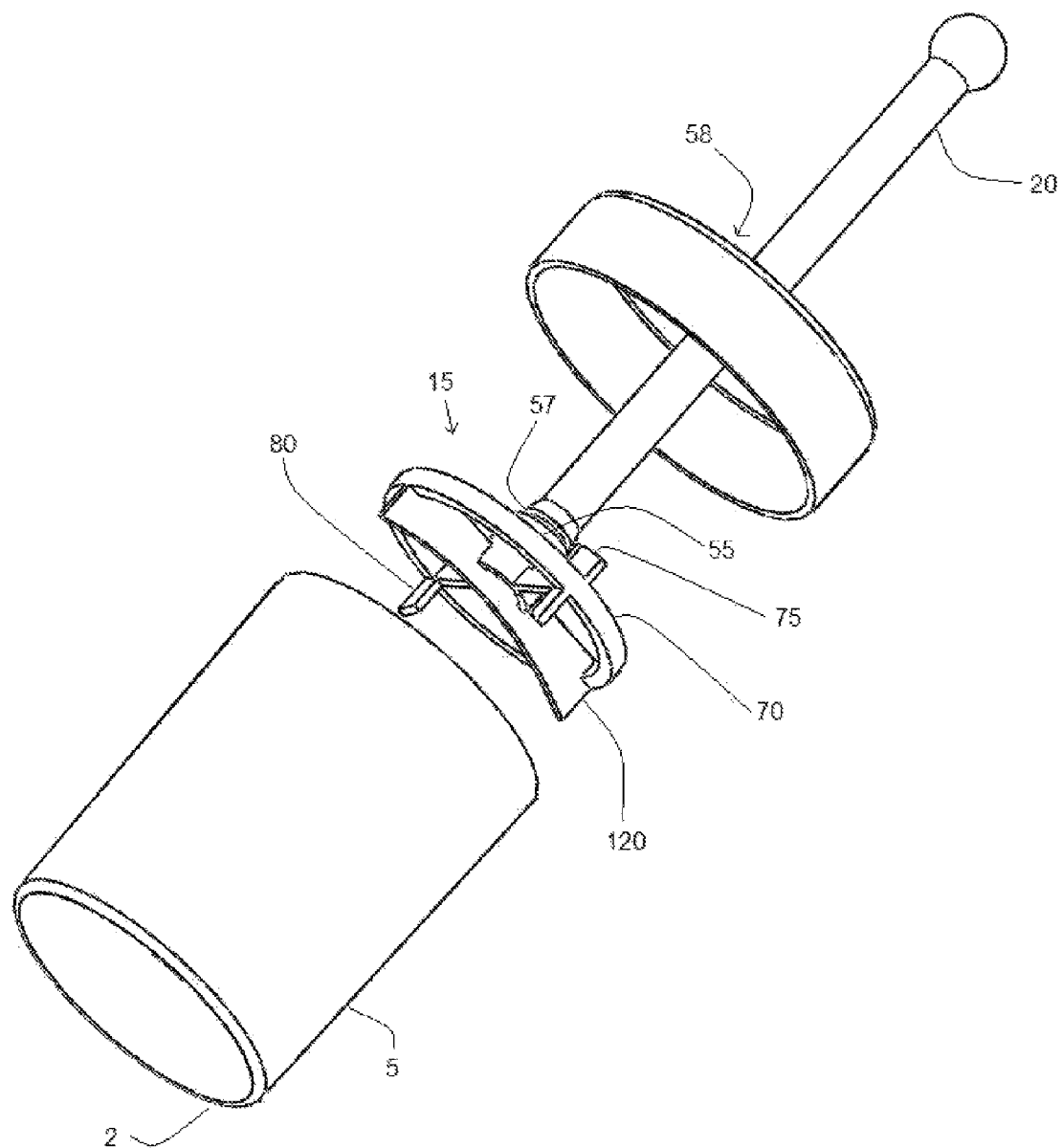
FIG. 4 depicts a perspective view of the mixing system of FIGS. 1 through 3.

FIG. 4 depicts a perspective view of the mixing element 15. As best seen in this view, the mixing element 15 includes a scraping paddle 120 which desirably extends from the lower end of the central shaft 55 and outward to the collar 70. The lower surface of the scraping paddle 120 desirably follows and/or compliments the interior surface of the distal end 2 of the receptacle 5, such that the surface wipes or scrapes against the receptacle inner surface and/or bottom surface, desirably mixing and/or partially mixing material adjacent the inner surface of the receptacle 5. As previously noted, a pair of flanges 80 extend downward from the collar 70 at positions intermediate the scraping paddle 120. A pair of upper flanges 75 extend upward from the collar 70 and desirable incorporate at least one wiping surface adjacent the inner surface of the receptacle 5 to desirably urge unmixed and/or partially mixed material back towards the center of the receptacle 5.

In other alternative embodiments, the mixing element 15 could incorporate various other sized of flanges and/or axle/rim arrangements (not shown).

Larger mixing surfaces may reduce the amount of mixing required (i.e., number of rotations of the mixing element), but may also allow the components to "ride up" the mixing element 15. In such a case, the mixing process might require a momentarily pause in order to allow the components to fall back into the mixture. To avoid such interruption, the upper flanges 75 can be provided with a minimum sufficient surface area to move sufficient amounts of mixed material back towards the center of the receptacle 5.

Desirably, the mixing element 15 is sized to extend substantially across the interior of the receptacle 5. As previously noted, such an arrangement can facilitate mixing of the powder and liquid components, because rotation of the mixing element 15 will allow components to "wipe" or "scrape" the powdered and liquid components off the inner walls of the receptacle, ensuring even mixing of the components. While actual physical contact between the side walls of the receptacle 5 and the components of the mixing element 15 are not absolutely necessary, in least one embodiment the mixing element 15 and the interior walls of the receptacle 5 are in very close proximity.

In the various embodiments described herein, sufficient mixing of poly(methyl-methacrylate) bone cement, comprising a powdered material with a liquid monomer, can be accomplished in less than 30 seconds, with as little as 20 full rotations of the mixing element 15 within the receptacle 5.

If desired, electrical or mechanical mixing devices can be used in conjunction with the present invention to assist with rotation of the mixing element 15. Such devices can include electric drills and/or mechanical or gear-driven mixing devices. In addition, a vacuum-powered or "turbine powered" mixing head could be attached to the device in a known manner to assist with rotation of the mixing element 15 and mixing of the desired material. Such vacuum-assisted mixing devices could, in various embodiments, also be utilized to remove fumes and/or degas the material while mixing.

C. The Plunger/Dispensing Element

Once the mixing element 15 and mixing cap 30 have been removed from the receptacle 5, a plunger and dispensing unit 200 can be introduced into the receptacle 5.

Figure 5:
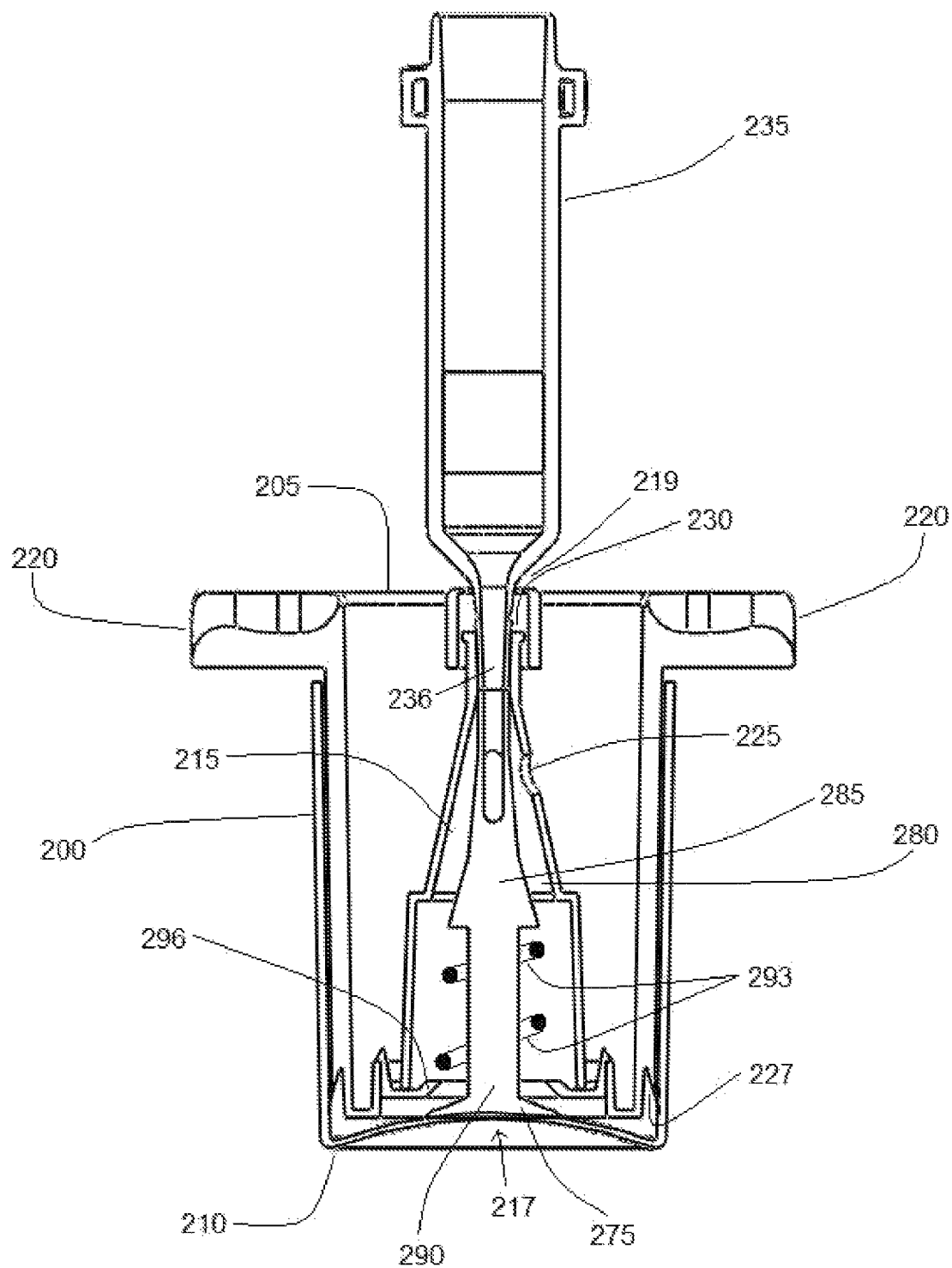
FIG. 5 depicts a cross-sectional view of one alternate embodiment of a dispensing and transfer system and associated receptacle constructed in accordance with an embodiment of the present invention.
Figure 6:
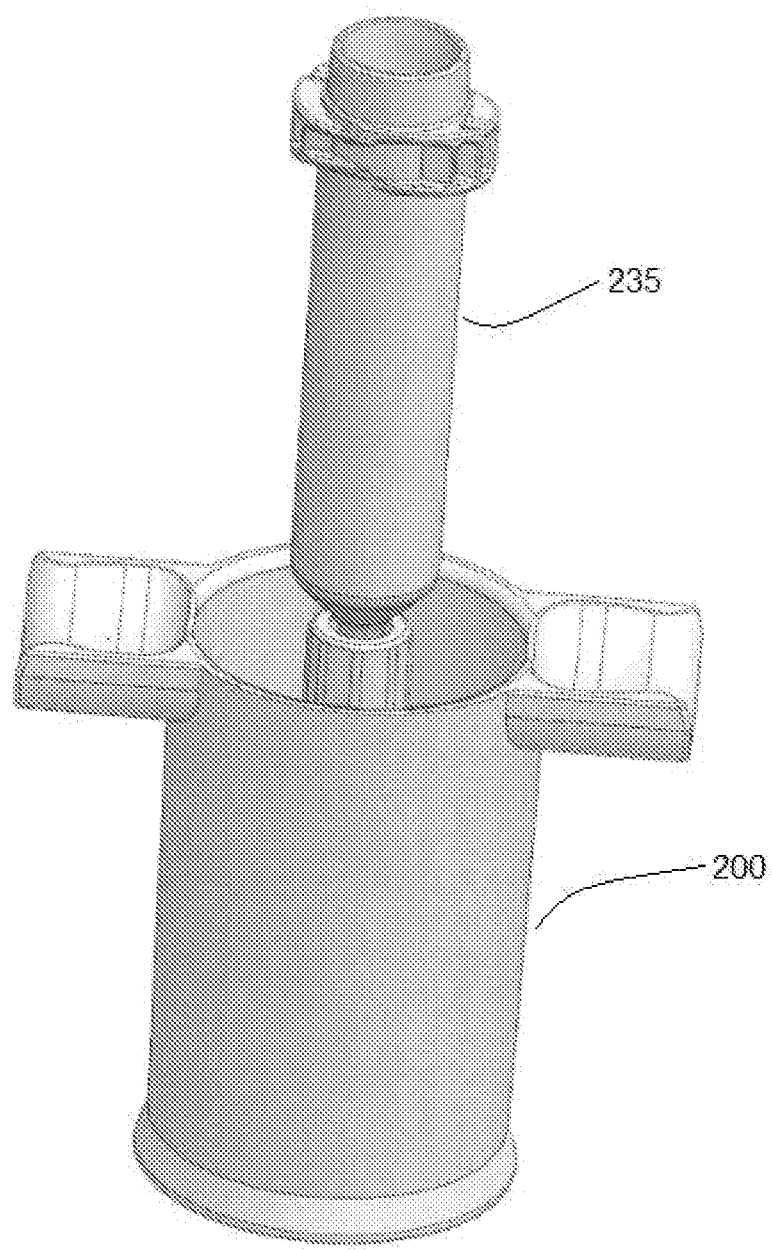
FIG. 6 depicts a perspective view of the plunger of FIG. 5.

FIG. 5 depicts one embodiment of the present invention for use with various surgical deployment instruments, including syringes. In this embodiment, the syringe body is filled or "loaded" with PMMA through its distal tip 236 or luer-side opening. The plunger comprises a cylindrical body 200 having an upper end 205 and a lower end 210. The body 200 is desirably hollow, with a lumen 215 extending from a lower opening 217 in the lower end 210 to a dispensing opening 219 proximate the upper end 205. A pair of handles 220 are attached to the upper end 205 of the body 200.

The plunger 200 is desirably sized and configured to fit into the interior bore of the receptacle 5. A flexible seal 227 is formed or positioned on the lower end 210 of the body 200. Seal materials could include, but are not limited to, non-rigid materials that are relatively unaffected by contact with the mixed bone filling material. In use, the flexible seal 227 desirably seals the plunger 200 within the receptacle 5 and prevents the mixed material from passing between the plunger 200 and the inner wall of the receptacle 5 as the plunger 200 is advanced. The seal also desirably prevents the release of fumes from the receptacle.

The first lower opening 217 is desirably formed in the lower end 210 of the plunger 200, and communicates directly with through the lumen 215 with the upper opening 219. An air bleeder component 225 may be attached to the lumen 215. A LUER® fitting 230 or other securing and/or sealing arrangement is positioned around the upper opening 219. In the present embodiment, a dispensing syringe 235 is secured to the luer fitting 230. Of course, any number of other types of fittings or tubings could be incorporated, depending upon the type of instrument receiving the transferred mixed material.

The air bleeder component may comprise a valve with a small ball bearing (not shown) which allows air to escape as the plunger is advanced through the receptacle. The ball bearing (not shown) may be made from a plastic material that is less dense than the bone filling material. As the plunger contacts the viscous bone filling material, the ball bearing is forced up into a closed position in a known manner. In various embodiments, purging of the air allows for direct contact between the plunger and material, which provides for improved dispensing control of the material. The valve may also comprise a flap or other arrangement (not shown), attached to a valve body by a living hinge or other arrangement, with the flap pushed shut by PMMA advancing through the valve.

After material mixing has been completed, and the mixing cap and mixing element removed from the receptacle 5, the distal tip 236 of the syringe 235 is attached to the plunger 200 and the plunger 200 is advanced into the receptacle 5. Initial advancement of the plunger 200 within the receptacle 5 will desirably expel air through the lumen 215, which either exits through the air bleeder component 225 (i.e., a valve that can automatically purge the air in the receptacle between the plunger and mixed bone filling material) or through the syringe 235 attached to the luer fitting 230. If desired (and generally depending upon the size of the plunger and receptacle), as the plunger 200 is introduced into the receptacle 5, the entire unit can be gripped and squeezed with a thumb on each plunger handle 220 and the index, middle and/or ring fingers of both hands placed under the receptacle 5, squeezing the plunger into the receptacle and transferring the mixed material from the receptacle 5 into the syringe 235.

Alternatively, for smaller receptacle and plunger combinations (such as, for example, where 5 cc or less of mixed material is desired), the plunger and receptacle can be sized and arranged such that they can be gripped and squeezed using a single hand, with a thumb in contact with the base of the receptacle and the index and middle fingers each contacting one of the handles 220, dispensing the material into the syringe and/or directly into a targeted anatomical location (or other area) through an extension tube (not shown) or other dispensing arrangement extending outward of the plunger. In such an arrangement, the plunger and receptacle combination (with an extension tube) could be utilized similar to a dispensing syringe.

Once the lower end 210 of the plunger 200 contacts the mixed material, further advancement of the plunger 200 will urge the mixed material into the lower opening 217, through the lumen 215 and into the syringe 235 through the upper opening 219 and luer fitting 230. Desirably, the air bleeder component 225 will allow air and/or other vapors to exit the lumen 215, but will close or otherwise prevent mixed material from exiting the lumen 215 through the component 225. If desired, an activated charcoal filter or other filtering device (not shown) may be incorporated onto the air bleeder component, or the component may be attached to the operating room vacuum system. Desirably, the plunger 200 is advanced until all mixed material has been dispensed into the syringe and/or until the syringe is filled. In various embodiments, the syringe may be a 5 cc, 10 cc, 20 cc or 50 cc syringe, although any size syringe may be appropriate, depending upon the amount of material mixed.

Once a desired amount of material has been dispensed into the syringe, the plunger and receptacle may be inverted and the syringe removed, with removal of the syringe allowing the spring to close off the plunger opening 217. Additional syringes (if desired) may be attached to the luer fitting 230, the plunger/receptacle placed upright, and additional material dispensed in subsequent steps. If desired, the lower surface 210 of the plunger 200 can be formed in a curved or arcuate surface to compliment a bottom surface of the receptacle, or the bottom surface of the receptacle can be formed in a flat shape.

Once dispensing of mixed material is complete, a cap (not shown) can be placed on the luer fitting 230, and the receptacle 5 and plunger 200 disposed of appropriately.

Figure 7:
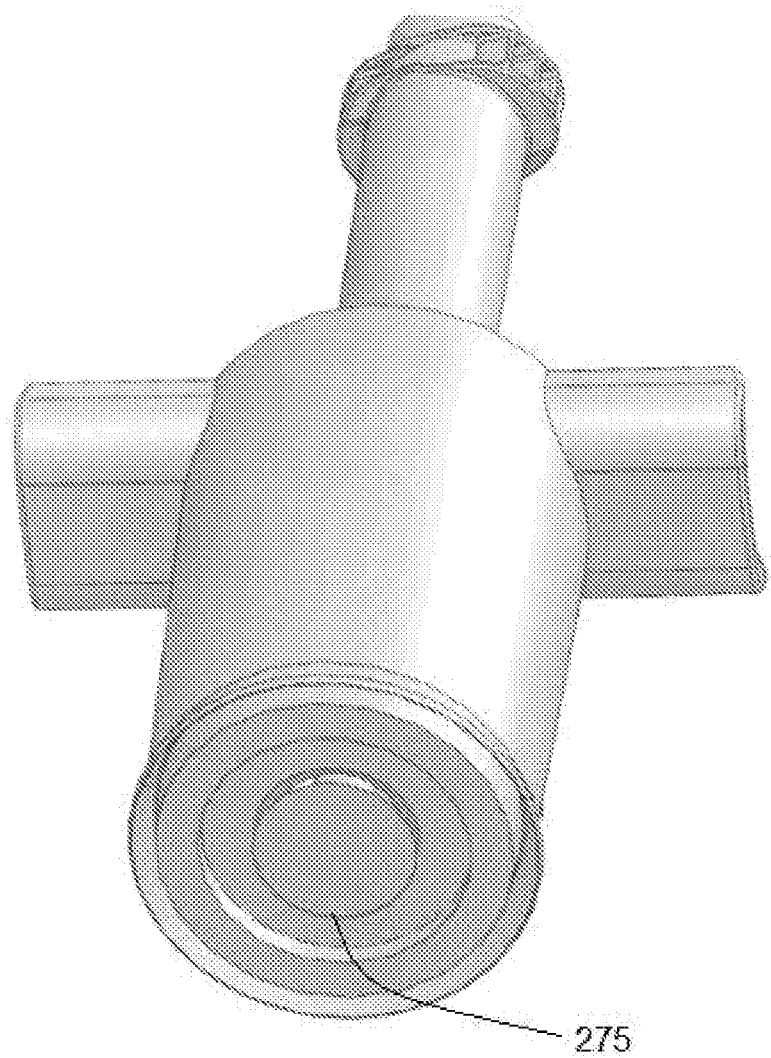
FIG. 7 depicts a bottom perspective view of the plunger of FIG. 5.
Figure 8:
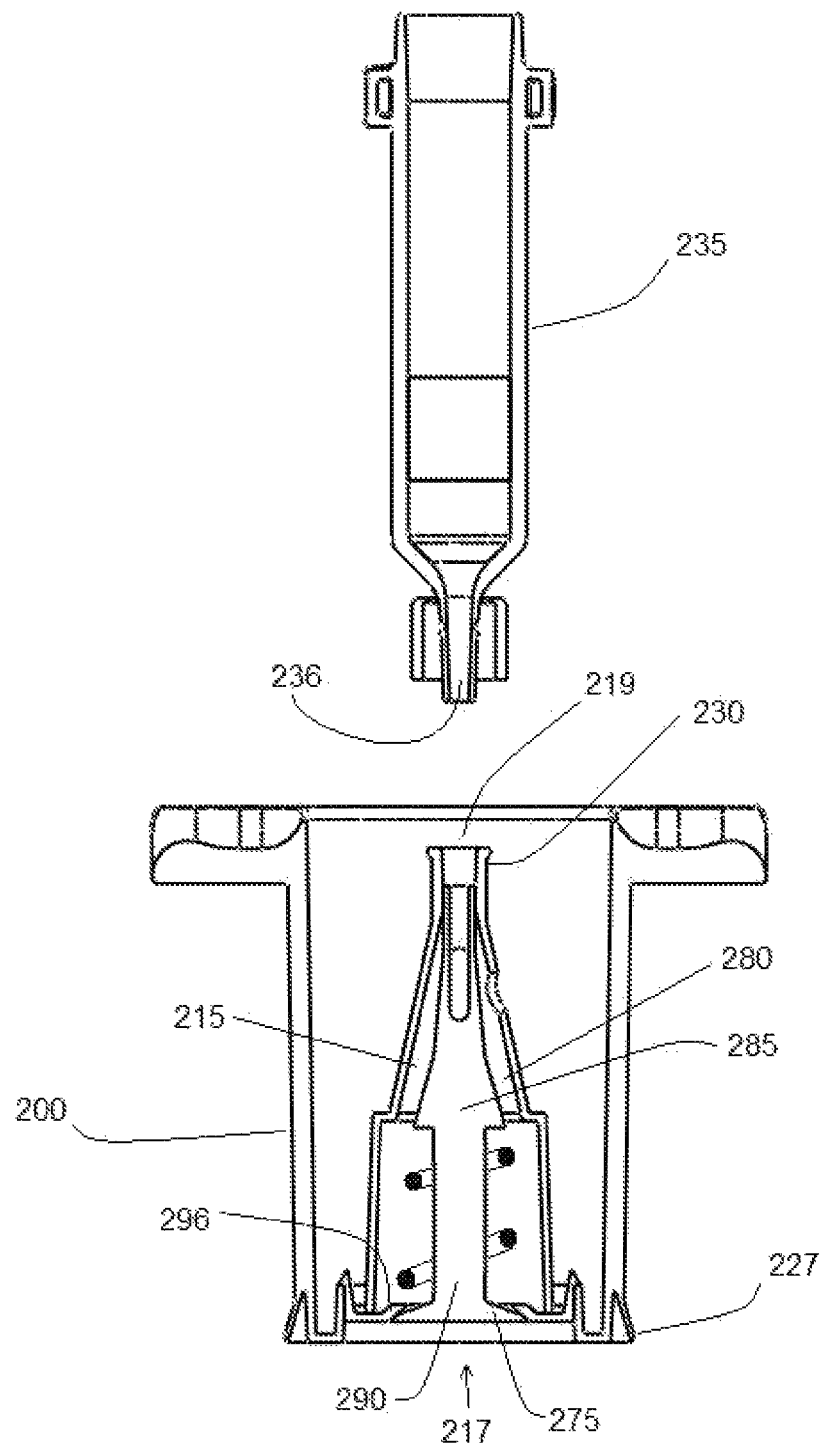
FIG. 8 depicts a cross-sectional view of the plunger of FIG. 5, with the syringe undocked and a closed valve.
Figure 9:
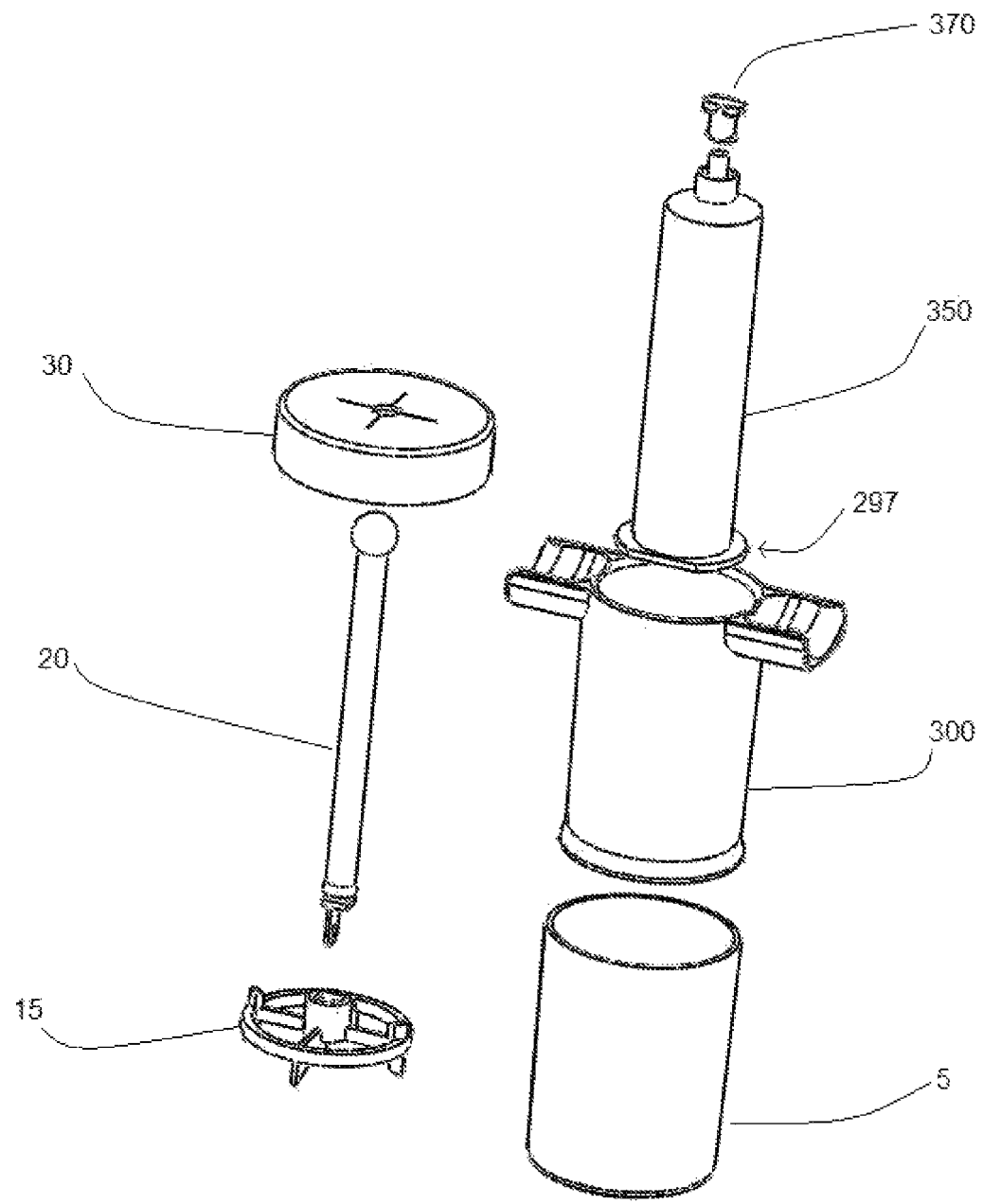
FIG. 9 depicts a side perspective view of one embodiment of a mixing, dispensing and transfer system in kit form.
Figure 10:
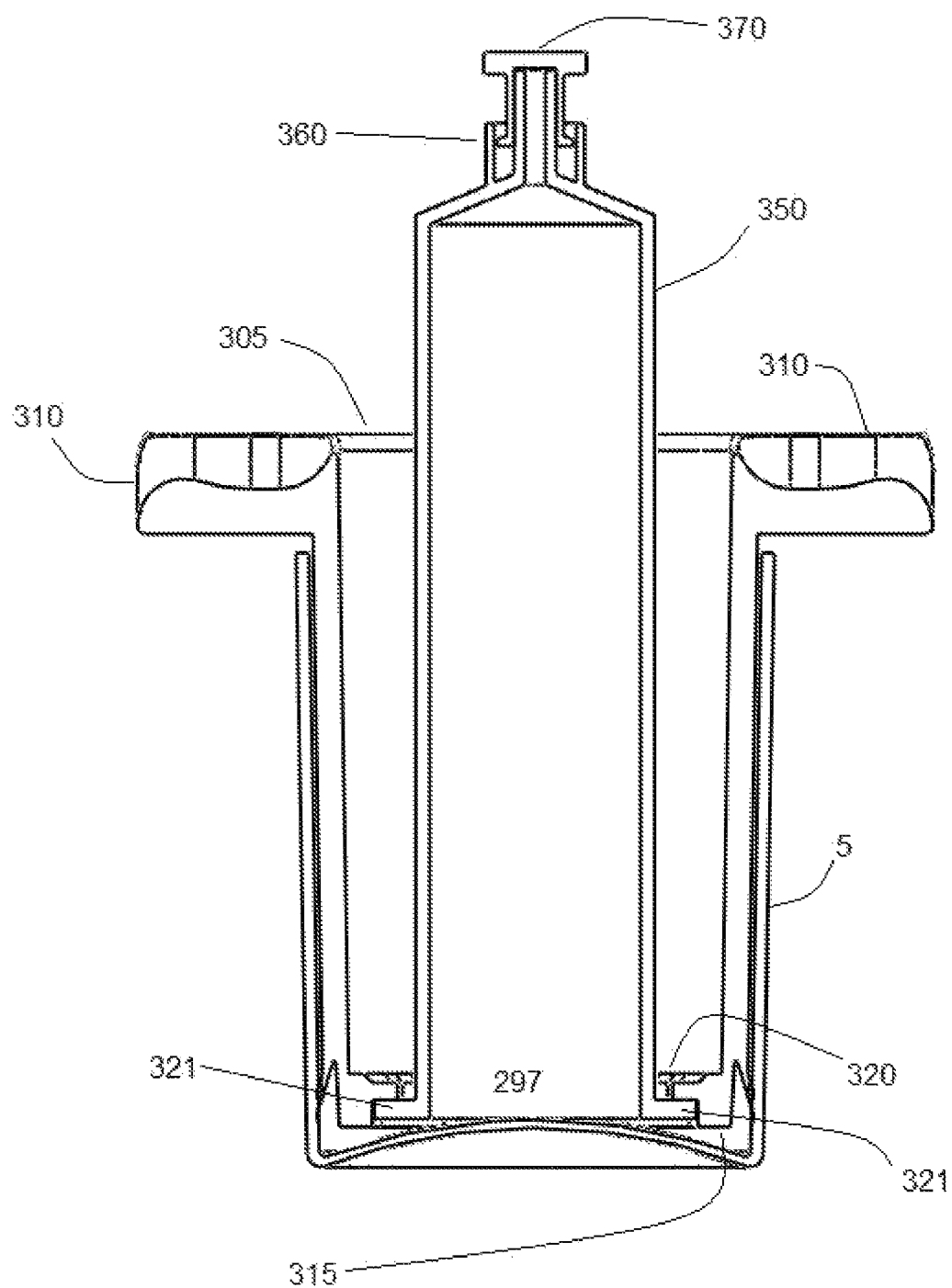
FIG. 10 depicts a cross-sectional view of the dispensing and transfer system of FIG. 9.

If desired, the lower opening 217 of the plunger 200 can incorporate a valve 275 or similar arrangement that selectively opens and closes to allow or prohibit access to the lumen 215. In one embodiment, best seen in FIGS. 5, 7 and 8, the lumen incorporates a valve component 280 having a central shaft 285, a valve body 290 and a return spring 293. A valve seat 296 is formed on an inner surface 298 of the lower opening 217. In use, the valve 275 can be opened by attachment of the syringe 235 to the luer fitting 230 (or if desired, the valve can be manually actuated by pushing downward on the syringe), which forces distal tip 236 of the syringe 235 in contact with the central shaft 285, which urges the valve body 290 away from the valve seat 296 and allows mixed material to enter the lumen 215 and travel up into the syringe 235. When the syringe 235 is separated from the luer fitting 230, the return spring 293 urges the valve body 290 into contact with the valve seat 296 and the valve 275 closes, thereby inhibiting leakage of any remaining PMMA from the receptacle 5. Additional syringes may be attached for further PMMA dispensing, and once dispensing is complete, removal of the final syringe will desirably close the valve 275 and seal the system for disposal, as desired.

FIGS. 9 through 14 depict an alternate embodiment of a plunger 300 for use in filling or "loading" an alternative dispensing syringe 350 from the proximal end 297 or "piston side" of the syringe 350. In this embodiment, the plunger 300 includes a cylindrical body 305 having an upper end 310 and a lower end 315, the upper end being open, and the lower end having a docking collar 320 for engaging a flange 321 or other portion of the first end of a large-diameter dispensing syringe 350 (i.e., a 10 cc, 20 cc or larger syringe). One or more flanges 325 are attached to the upper end 310. In this embodiment, flanges (not shown) on the syringe 350 are engaged directly to the docking collar 320, and advancement of the plunger allows mixed material to enter an opening 317 on the lower end 315 of the plunger 300 and directly enter the first end of the syringe 350. In this embodiment, an air bleeder component is not absolutely necessary, although one could be incorporated, if desired. As the plunger 300 is advanced into the receptacle 5, air travels through the opening (not shown) on the lower end 315 of the plunger 300 and passes through the syringe 350, exiting through the distal luer tip 360 of the syringe 350. As the plunger continues to advance, mixed material will be pushed through the opening (not shown) on the lower end 315 of the plunger 300 and passes into the syringe 350. When sufficient material has entered the syringe, or when material begins to exit the distal luer tip 360. A cap 370 (FIG. 10) may be attached to the distal luer tip 360, the receptacle and plunger assembly is inverted, and the syringe released from the docking collar 320. The receptacle and plunger assembly may then be discarded. If desired, a sealing cap (not shown) may be provided that secures to the upper end 310 of the plunger 300 and seals the system for appropriate disposal.

Figure 11:
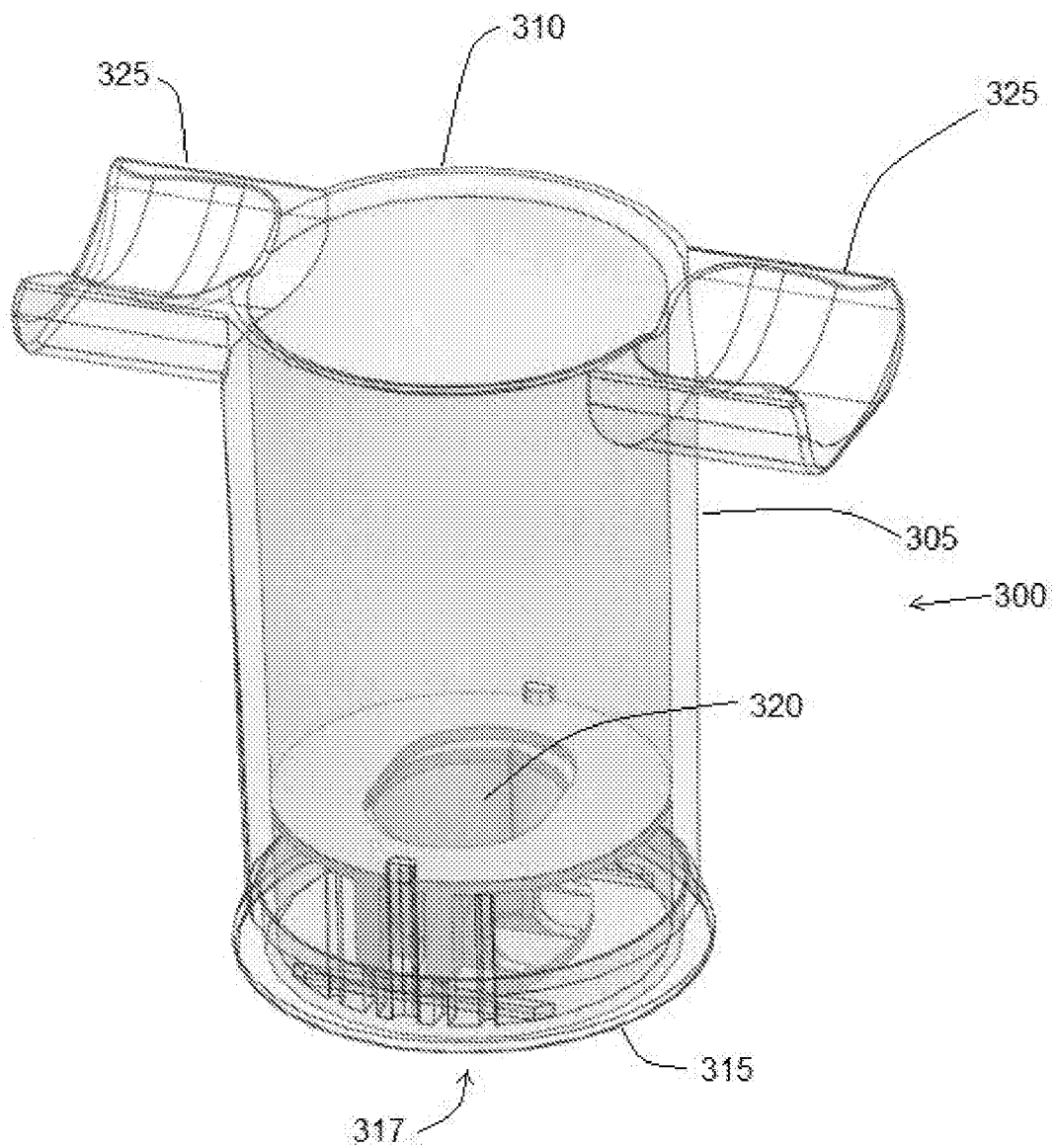
FIG. 11 depicts a perspective view of an alternate embodiment of a dispensing and transfer plunger for accepting a proximal end of a syringe.
Figure 12:
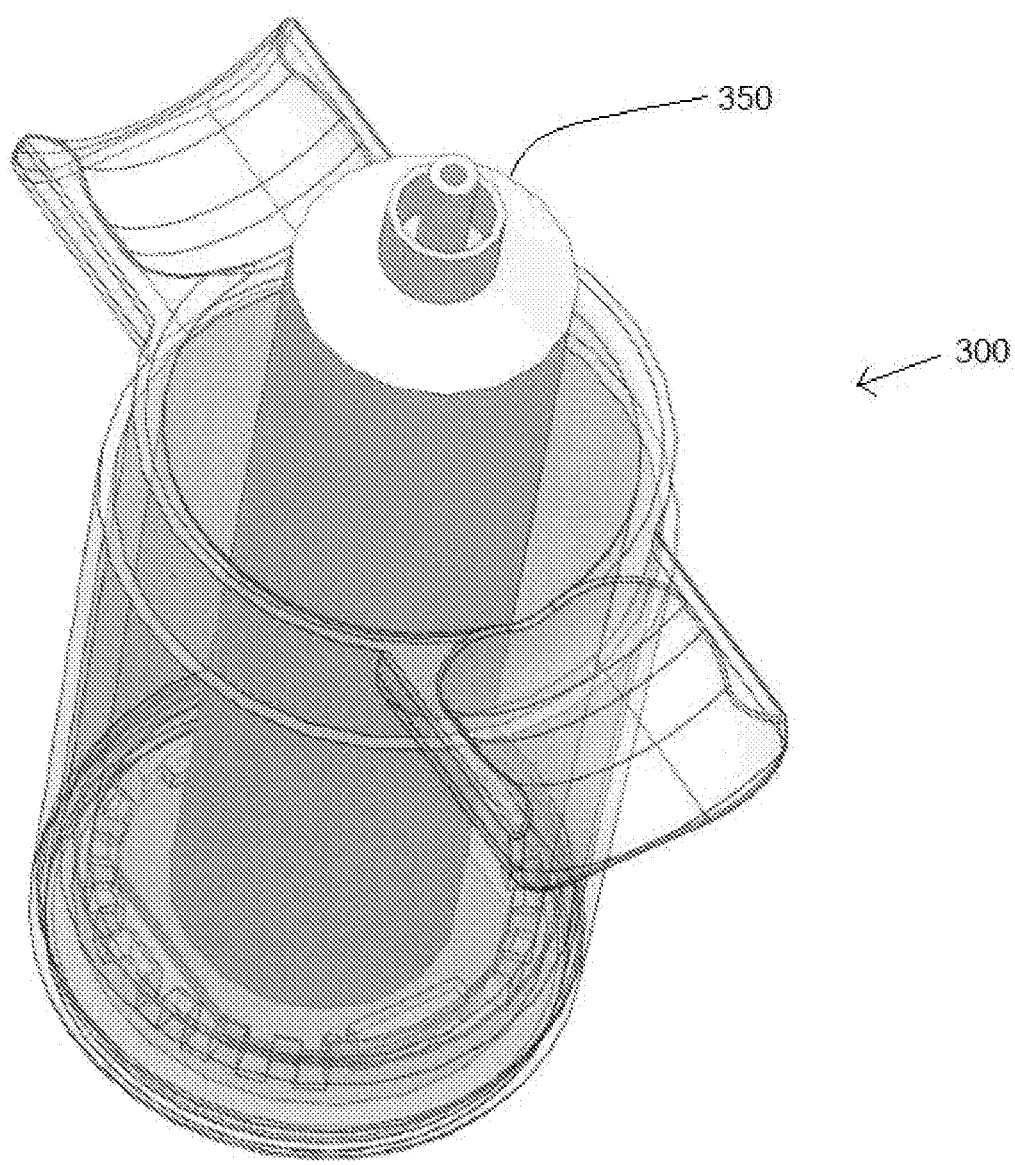
FIG. 12 depicts a perspective view of the dispensing and transfer system of FIG. 10.
Figure 13:
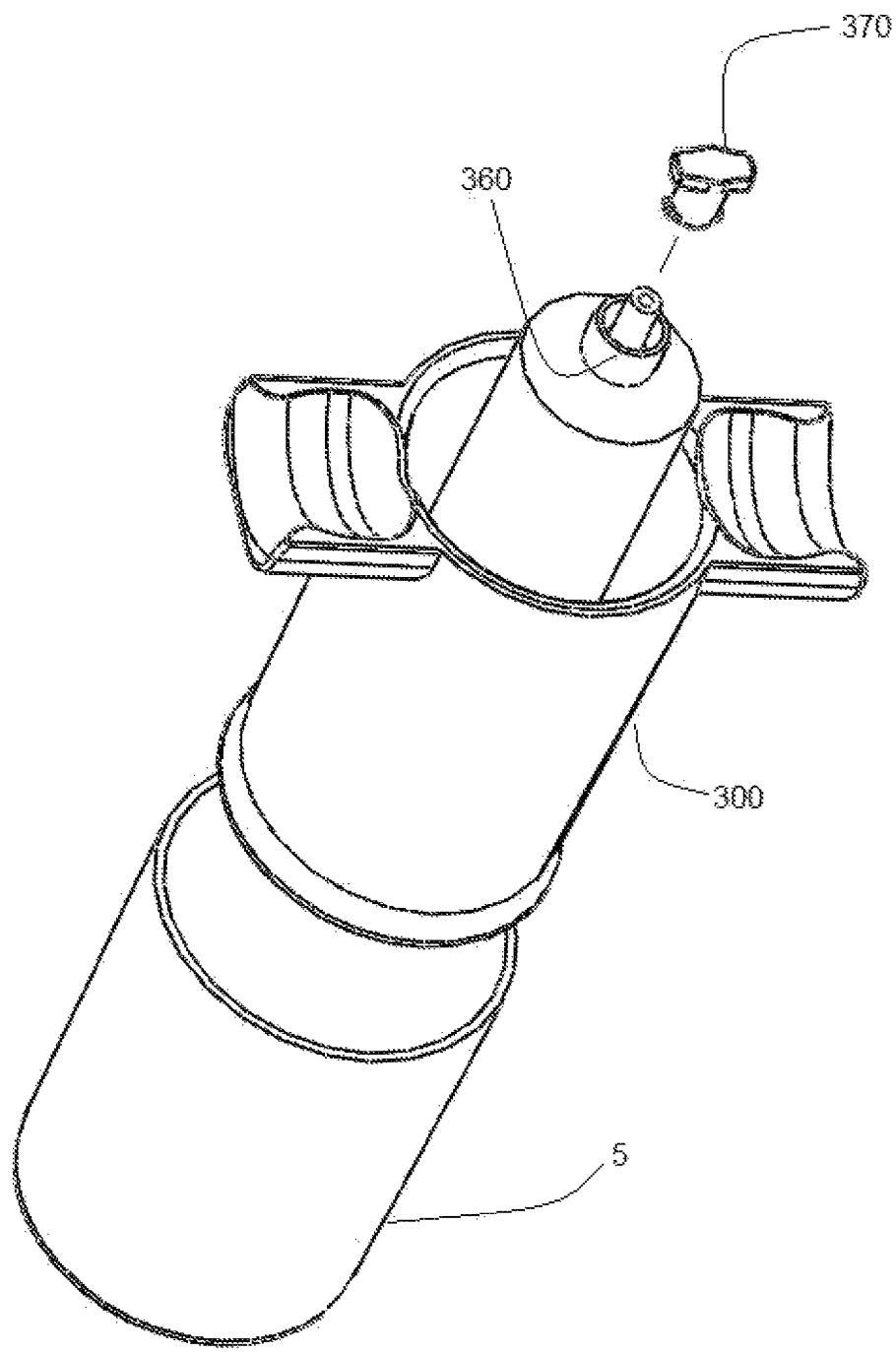
FIG. 13 depicts a perspective view of the dispensing and transfer system of FIG. 9.
Figure 14:
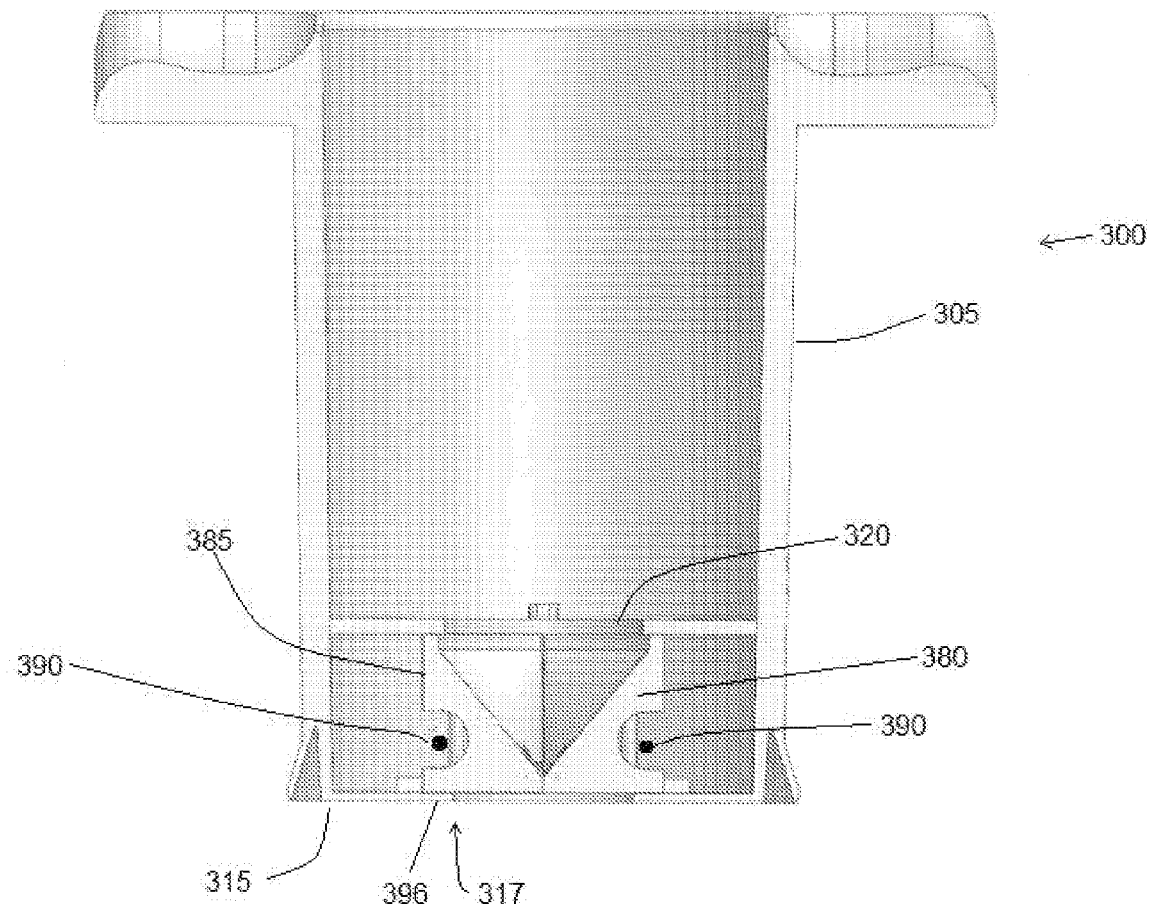
FIG. 14 depicts a cross-sectional view of the plunger of FIG. 11.

If desired, the docking collar 320 of the plunger 300 could incorporate a lower opening 317 having a valve 375 or similar arrangement that selectively open and closes to allow or prohibit access to the syringe. FIG. 11 depicts a docking collar 320 incorporating a valve component 380 having a central body 385 and a return spring 390. A valve seat 396 is formed on a inner surface (not shown) of the lower opening 317. In use, the valve 375 can be opened by engaging one or more rotation flanges (not shown) on the syringe with the docking collar 320, pushing downward on the central body 385, which separates the central body 385 from the valve seat 396 and allowing mixed material to enter the docking collar 320 and travel into the syringe. When the syringe is released (after the system has desirably been inverted), a return spring 393 urges the central body 385 against the valve seat 396 and the valve 375 closes, desirably inhibiting any leakage of any remaining PMMA material from the dispensing unit. If desired, another syringe may be attached to the unit, opening the valve 375 for further dispensing of PMMA. Once all dispensing has been completed as desired, the removal of the syringe seals the unit for disposal.

In various embodiments, the return spring 393 could comprise a metallic or molded plastic element, formed either separately or integrally with the plunger 300 or other components of the valve. In various other embodiments, the return spring could comprise a flexible or other type of element, or could be some other arrangement known in the art to bias a valve or other flow control device to either an open or closed position, as desired.

The various embodiments of the present invention provide for an inexpensive, easily manufactured mixing and dispensing/transfer system that provides for reduced monomer fume emissions in an easy to use system resulting in little mess and/or disposal issues. The system allows for either right- or left-handed operation of the system. In addition, the disclosed system facilitates transfer of a majority of the mixed material into the surgical dispensing device with little wastage (i.e., when dispensing is complete there is little of the mixed PMMA remaining within the receptacle and/or within the tubes leading to the syringe), thereby reducing the amount of PMMA component material(s) required for a given surgical procedure.

In one embodiment, the receptacle, stand, mixing element, mixing cap, plunger, measuring devices and syringes, as well as the components to be mixed, are gathered together for use, or are withdrawn as needed from a kit. The kit may include instructions for use. For medical applications, the mixing and application device is typically supplied in sterilized, ready-fitted-together structural units, although the system may also be packaged and/or shipped in an unassembled form.

In use, a physician or other individual may assemble the various components of the kit (if desired and/or necessary), and then may use a measuring device to measure a component to be mixed, such as a powdered component for acrylic (polymethylmethacrylate) bone cement. The powdered component is poured into the receptacle. If the receptacle bears a graduated scale or other measuring scale(s) on its outer or inner surfaces, the component can be added to the receptacle until the desired level is reached. After the powdered component is added to the receptacle, another component, such as a liquid monomer for bone cement, is added.

The mixing element and mixing cap are then obtained, and the mixing element is inserted into the receptacle. The mixing cap is secured to the receptacle, and the physician turns the knob or otherwise activates a device connected to the mixing element to mix the material. The knob may be rotated back and forth, first clockwise and then counterclockwise, e.g. (or vice versa), by half-turns, relative to the receptacle. Alternatively, or in conjunction with this back and forth motion, the knob may be rotated in a single direction. In conjunction, the knob may be advanced and withdrawn relative to the mixing cap, moving the mixing element longitudinally within the receptacle. Desirably, the knob is rotated enough times to adequately mix the mixture. Once mixing is complete, the mixing cap can be released and/or removed and the mixing element withdrawn from the receptacle (with the mixing element desirably "locked" or otherwise secured within the cap). The mixing cap and mixing element are discarded appropriately.

The plunger assembly is then placed into the receptacle, and advanced. A syringe is secured to the plunger, and further advancement of the plunger into the receptacle urges mixed material through the plunger and into the syringe. Multiple syringes may be filled, and when dispensing is completed, the plunger and receptacle may be discarded appropriately.

The present system is particularly advantageous with the mixing and transfer of PMA bone cement, where the release of fumes and/or vapors from a surgical material is undesirable and it may be advantageous to use a closed mixing and transfer system for the preparation and/or delivery of medical materials such as bone cement. For example, the fumes and/or vapors from the liquid monomer component of PMMA bone cements can have a very unpleasant smell and inhalation of these fumes may pose a significant health risk to various operating room personnel as well as the patient.

In the case of bone cement comprising PMMA powder and liquid monomer components, the liquid monomer is typically sealed within a glass jar or ampoule prior to use while the powder is contained in a plastic bag. One example of such packaging is found with SimplexP® PMMA bone cement, commercially available from Howmedica Corporation. While the powdered component of such bone cement is generally inert and not prone to becoming airborne (unless sufficiently disturbed), the liquid monomer component has a very low vapor pressure and vaporizes readily in contact with air.

Once a glass ampoule containing liquid monomer is opened (typically by breaking the frangible cap on the glass ampoule) the liquid monomer is exposed to the atmosphere and begins to vaporize immediately. Moreover, during the mixing process, the liquid monomer continues to vaporize and also outgasses from the liquid/powder mixture. Once mixing is completed, the monomer continues to outgas from the liquid/powdered mixture, until such time as the mixture is contained within an enclosed environment (such as a syringe or other closed dispensing device or when the mixture is placed within the patient's body). Unless the mixture is contained within an enclosed environment during substantially all of the steps of the mixing and delivery operation, therefore, a significant amount of vaporized monomer may be released to the operating room during mixing and dispensing of bone cement.

By containing the various components of the mixed material within a closed environment, and by quickly and securely enclosing any exposed mixing material, the present invention significantly reduces the amount of monomer and/or other toxic materials released into the operating room environment, and does not absolutely require the use of auxiliary vacuum sources, etc., in attaining the reduced fume emissions. With this embodiment the PMMA mixture can be dispensed from the mixing and dispensing system without significant release of monomer fumes. Once dispensing is complete the entire closed system may be disposed of safely.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims equivalents thereof.

The features of the invention are set forth in the following claims:

The invention claimed is:

1. A system comprising:
   a receptacle having a sidewall peripherally surrounding an interior for receiving components of a bone filling material in an unmixed condition, the receptacle including a first end region and a second end region oppositely spaced from the first end region, the receptacle including a threaded region proximate to the first end region, the second end region comprising a base for supporting the first end region in an upright condition;
   a mixing element sized for insertion into the interior of the receptacle through the first end region to mix the components of the bone filling material within the interior of the receptacle, the mixing element also being sized for withdrawal from the interior of the receptacle through the upright first end region after mixing of the components;
   a mixing cap for engaging the first end region of the receptacle, the mixing cap including a locking mechanism for selectively engaging and securing the mixing element within the cap; and
   a plunger sized for insertion, after withdrawal of the mixing element, into the interior of the receptacle through the first end region for advancement through the interior toward the second end region, the plunger having an internal lumen extending at least partially there through, with a dispensing opening located within the plunger and in fluid communication with the lumen, the plunger dispensing the mixed components of the bone filling material through the dispensing opening as the plunger is advanced towards the second end region.

2. A system comprising:
   a receptacle having a sidewall peripherally surrounding an interior for receiving components of a bone filling material in an unmixed condition, the receptacle including a first end region and a second end region oppositely spaced from the first end region, the second end region comprising a base for supporting the first end region in an upright condition;
   a mixing element sized for insertion into the interior of the receptacle through the first end region to mix the components of the bone filling material within the interior of the receptacle, the mixing element also being sized for withdrawal from the interior of the receptacle through the upright first end region after mixing of the components; and
   a plunger sized for insertion, after withdrawal of the mixing element, into the interior of the receptacle through the first end region for advancement through the interior toward the second end region, the plunger having an internal lumen extending at least partially there through, with a dispensing opening located within the plunger and in fluid communication with the lumen, the plunger dispensing the mixed components of the bone filling material through the dispensing opening as the plunger is advanced towards the second end region, the plunger further comprises an air purging valve positioned within the plunger and in fluid communication with the lumen.

3. The system according to claim 2 further comprising a syringe having a fitting for engaging the dispensing opening and receiving the mixed bone filling material.

4. The system according to claim 2, the plunger further comprising a valve positioned within the plunger and in fluid communication with the dispensing opening, the valve normally in a closed condition and connected to an attachment fitting arranged and configured such that the valve is selectively maintained in an open condition when a surgical device is attached to the attachment fitting.

5. A system comprising:
   a receptacle having a sidewall peripherally surrounding an interior for receiving components of a bone filling material in an unmixed condition, the receptacle including a first end region and a second end region oppositely spaced from the first end region, the second end region comprising a base for supporting the first end region in an upright condition;
   a mixing element sized for insertion into the interior of the receptacle through the first end region to mix the components of the bone filling material within the interior of the receptacle, the mixing element also being sized for withdrawal from the interior of the receptacle through the upright first end region after mixing of the components; and
   a plunger sized for insertion, after withdrawal of the mixing element, into the interior of the receptacle through the first end region for advancement through the interior toward the second end region, the plunger having an internal lumen and a valve, the valve in fluid communication with the internal lumen, the valve connected to an attachment fitting arranged and configured such that the valve is selectively maintained in an open condition when a surgical device is attached to the attachment fitting, and the valve is selectively maintained in a closed condition when a surgical device is not attached to the attachment fitting, the plunger further having a dispensing opening for dispensing the mixed components of the bone filling material through the dispensing opening as the plunger is advanced towards the second end region.

6. The system of claim 5, wherein the dispensing opening is located inside of the plunger.

7. The system of claim 5, wherein the plunger further comprises an air purging valve positioned within the plunger and in fluid communication with the lumen.

8. The system of claim 5, further comprising a syringe having a fitting for engaging the dispensing opening and receiving the mixed bone filling material.

9. The system of claim 5, further comprising a mixing cap for engaging the first end region of the receptacle, the mixing cap including a capture mechanism for selectively engaging the mixing element within the cap.

10. The system according to claim 2, further comprising a cap for engaging the first end region of the receptacle, the cap including a locking mechanism for securing the cap to the receptacle.

11. The system according to claim 1, wherein the threaded region proximate to the first end region is a threaded region formed on an interior surface of receptacle.

12. The system according to claim 1, wherein the threaded region proximate to the first end region is a threaded region formed on an exterior surface of the receptacle.

13. The system according to claim 1, wherein a bore of the receptacle is of a constant diameter.

14. The system according to claim 1, wherein a bore of the receptacle is circular.

15. The system according to claim 1, wherein the mixing cap further comprises a threaded cap region for engaging with the threaded region of the receptacle.

16. The system according to claim 15, wherein the cap includes at least one opening formed in the cap.

17. The system according to claim 1, wherein at least a portion of the receptacle comprises a transparent material.

18. The system according to claim 11, wherein the threaded region extends at least partially between the first and second end regions.

19. The system according to claim 12, wherein the threaded region extends at least partially between the first and second end regions.

\* \* \* \* \*